United States Patent
Safai et al.

(10) Patent No.: US 7,902,524 B2
(45) Date of Patent: Mar. 8, 2011

(54) PORTABLE CORROSION DETECTION APPARATUS

(75) Inventors: Morteza Safai, Seattle, WA (US); Gary E. Georgeson, Federal Way, WA (US)

(73) Assignee: The Boeing Company, Chicago, IL (US)

( * ) Notice: Subject to any disclaimer, the term of this patent is extended or adjusted under 35 U.S.C. 154(b) by 119 days.

(21) Appl. No.: 12/390,965

(22) Filed: Feb. 23, 2009

(65) Prior Publication Data
US 2010/0213387 A1    Aug. 26, 2010

(51) Int. Cl.
G01N 21/64    (2006.01)
(52) U.S. Cl. .................................................. 250/458.1
(58) Field of Classification Search ............... 250/458.1, 250/372
See application file for complete search history.

(56) References Cited

U.S. PATENT DOCUMENTS

| | | | |
|---|---|---|---|
| 5,482,890 | A | 1/1996 | Liu et al. |
| 6,379,622 | B1 | 4/2002 | Polak et al. |
| 6,627,914 | B1 | 9/2003 | Komiyama et al. |
| 6,657,232 | B2 | 12/2003 | Morkoc |
| 6,717,664 | B2 | 4/2004 | Floyd et al. |
| 7,002,079 | B2 | 2/2006 | Mitchell et al. |
| 7,005,669 | B1 | 2/2006 | Lee |
| 7,342,235 | B1 * | 3/2008 | Harrison et al. ............... 250/372 |
| 7,528,372 | B2 * | 5/2009 | Garvey et al. .................. 250/330 |
| 2003/0160182 | A1 * | 8/2003 | Petrich et al. ............... 250/458.1 |
| 2004/0211894 | A1 * | 10/2004 | Hother et al. ............... 250/269.1 |
| 2004/0241424 | A1 | 12/2004 | Barbera-Guillem |
| 2004/0256612 | A1 | 12/2004 | Mohseni et al. |
| 2006/0152706 | A1 * | 7/2006 | Butland .......................... 356/71 |
| 2007/0048867 | A1 | 3/2007 | Farmer |
| 2007/0194297 | A1 | 8/2007 | McCarthy et al. |
| 2008/0050513 | A1 | 2/2008 | Wang et al. |
| 2008/0312847 | A1 | 12/2008 | Safai et al. |

FOREIGN PATENT DOCUMENTS

| | | | |
|---|---|---|---|
| WO | WO2005124340 A1 | 12/2005 |
| WO | WO2006107331 A1 | 10/2006 |
| WO | WO20061007493 A1 | 10/2006 |

OTHER PUBLICATIONS

U.S. Appl. No. 12/335,724, filed Dec. 16, 2008, Davis et al.
U.S. Appl. No. 12/390,983, filed Feb. 23, 2009, Safai et al.
Bakkers et al., Excited-State Dynamics in CdS Quantum Dots Adsorbed on a Metal Electrode, J Phys Chem B, vol. 103, No. 14, 1999, pp. 2781-2788.
"Making Nanodots Useful For Chemistry" Jun. 19, 2003, 1 page http://www.sciencedaily.com/releases/2003/06/030619075658.htm.

* cited by examiner

*Primary Examiner* — David P Porta
*Assistant Examiner* — Kiho Kim
(74) *Attorney, Agent, or Firm* — Yee & Associates, P.C.; Steven Corey

(57) ABSTRACT

A method and apparatus comprising a housing, an excitation unit, and a detector. The housing is portable and capable of being positioned relative to a location on an object. Quantum dots are present in the location. The excitation unit is mounted to the housing. The excitation unit is capable of sending energy into the location in which the energy is capable of causing a response from the quantum dots. The detector is mounted to the housing. The detector is capable of detecting the response from the quantum dots in the location.

29 Claims, 9 Drawing Sheets

PORTABLE CORROSION DETECTION APPARATUS

CROSS REFERENCE TO RELATED APPLICATION

The present disclosure is related to the following patent application entitled "Corrosion Detection and Monitoring System", Ser. No. 12/390,983; filed even date hereof, assigned to the same assignee, and incorporated herein by reference.

BACKGROUND INFORMATION

1. Field

The present disclosure relates generally to inspecting objects and, in particular, to a method and apparatus for nondestructive inspection of objects. Still more particularly, the present disclosure relates to a method and apparatus for inspecting an object using quantum dots associated with the object.

2. Background

Ensuring that external and/or internal surfaces of an object do not have any corrosion may be important during the manufacture, maintenance, and/or rework of objects, such as aircraft, aircraft structures, and/or parts for aircraft. Locations for an aircraft in which corrosion detection may be desired include, for example, without limitation, a cargo bay, a door sill, a landing gear bay, an insulation blank, a bilge, a seat track, a leading edge of a wing, a trailing edge of a wing, a trailing edge of a stabilizer, a fuel tank, and other suitable locations.

However, corrosion on an object may be hidden and/or masked underneath layers of paint or other coatings. Destructive corrosion detection is one technique for detecting corrosion. This technique involves removing paint and/or the disassembly of parts and assemblies to determine whether corrosion is present. These processes are destructive, slow, inefficient, and/or may be cost prohibitive.

Another type of inspection is nondestructive inspection. This type of inspection may be used without destroying, damaging, and/or disassembling the object. Currently available nondestructive corrosion inspection is performed visually using electromagnetic inspection, eddy current, and/or ultrasonic inspection methods. Eddy current and ultrasonic inspection measure material loss. Early detection of corrosion may be difficult depending on the amount and nature of the material loss.

Visual inspections may require a technician and/or other maintenance personnel to visually inspect all surfaces for signs of corrosion. These signs may include, for example, visible rust. However, visual inspections may miss corrosion in early stages. The technician and/or maintenance personnel may be unable to identify corrosion that may be present until the corrosion on a surface is substantial enough to be detected visually. Further, with the increasing complexity of aircraft structures and substructures, visual inspections may be more difficult without some disassembly.

These approaches may require more time, expense, inspections, and/or disassembly of the objects than would otherwise be desired for an early detection and monitoring capability.

Therefore, it would be advantageous to have an improved method and apparatus for nondestructive corrosion detection.

SUMMARY

In one advantageous embodiment, an apparatus comprises a housing, an excitation unit, and a detector. The housing is portable and capable of being positioned relative to a location on an object. Quantum dots are present in the location. The excitation unit is mounted to the housing. The excitation unit is capable of sending energy into the location in which the energy is capable of causing a response from the quantum dots. The detector is mounted to the housing. The detector is capable of detecting the response from the quantum dots in the location.

In another advantageous embodiment, a method is present for detecting corrosion on an object. A portable corrosion detection apparatus is positioned relative to a location on the object. Quantum dots are present in the location. Energy is sent into the location.

The features, functions, and advantages can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the advantageous embodiments are set forth in the appended claims. The advantageous embodiments, however, as well as a preferred mode of use, further objectives, and advantages thereof, will best be understood by reference to the following detailed description of an advantageous embodiment of the present disclosure when read in conjunction with the accompanying drawings, wherein:

DETAILED DESCRIPTION

Figure 1:
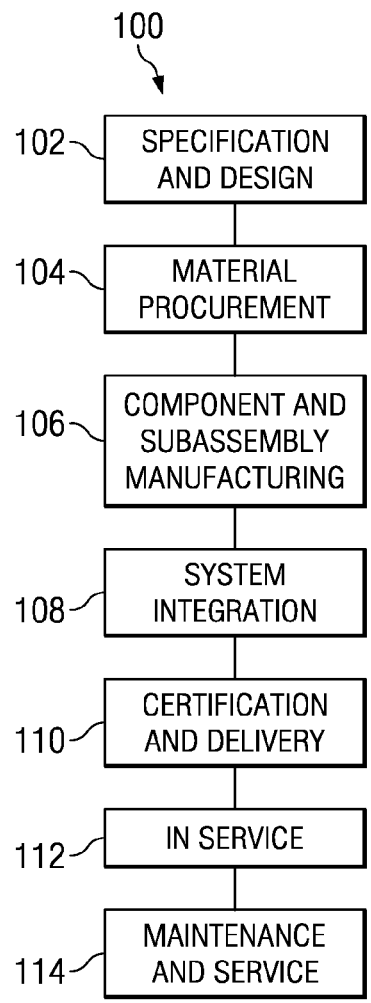
FIG. 1 is a diagram illustrating an aircraft manufacturing and service method in accordance with an advantageous embodiment.
Figure 2:
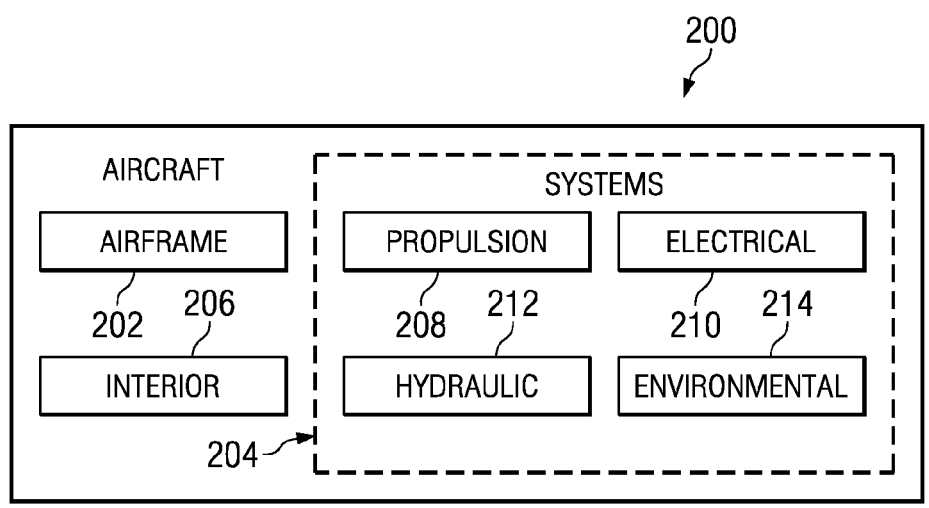
FIG. 2 is a diagram illustrating an aircraft in which an advantageous embodiment may be implemented.

Referring more particularly to the drawings, embodiments of the disclosure may be described in the context of aircraft manufacturing and service method 100 as shown in FIG. 1 and aircraft 200 as shown in FIG. 2. Turning first to FIG. 1, a diagram illustrating an aircraft manufacturing and service method is depicted in accordance with an advantageous embodiment. During pre-production, exemplary aircraft manufacturing and service method 100 may include specification and design 102 of aircraft 200 in FIG. 2 and material procurement 104.

During production, component and subassembly manufacturing 106 and system integration 108 of aircraft 200 in FIG. 2 takes place. Thereafter, aircraft 200 in FIG. 2 may go through certification and delivery 110 in order to be placed in service 112. While in service by a customer, aircraft 200 in FIG. 2 is scheduled for routine maintenance and service 114, which may include modification, reconfiguration, refurbishment, and other maintenance or service.

Each of the processes of aircraft manufacturing and service method 100 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of venders, subcontractors, and suppliers; and an operator may be an airline, leasing company, military entity, service organization, and so on.

With reference now to FIG. 2, a diagram of an aircraft is depicted in which an advantageous embodiment may be implemented. In this example, aircraft 200 is produced by aircraft manufacturing and service method 100 in FIG. 1 and may include airframe 202 with a plurality of systems 204 and interior 206. Examples of systems 204 include one or more of propulsion system 208, electrical system 210, hydraulic system 212, and environmental system 214. Any number of other systems may be included. Although an aerospace example is shown, different advantageous embodiments may be applied to other industries, such as the automotive industry.

Apparatus and methods embodied herein may be employed during any one or more of the stages of aircraft manufacturing and service method 100 in FIG. 1. For example, components or subassemblies produced in component and subassembly manufacturing 106 in FIG. 1 may be fabricated or manufactured in a manner similar to components or subassemblies produced, while aircraft 200 is in service 112 in FIG. 1.

Also, one or more apparatus embodiments, method embodiments, or a combination thereof may be utilized during production stages, such as component and subassembly manufacturing 106 and system integration 108 in FIG. 1, for example, without limitation, by substantially expediting the assembly of or reducing the cost of aircraft 200. Similarly, one or more of apparatus embodiments, method embodiments, or a combination thereof may be utilized while aircraft 200 is in service 112 or during maintenance and service 114 in FIG. 1.

For example, without limitation, advantageous embodiments may be used to inspect components during component and subassembly manufacturing 106 and system integration 108 of aircraft 200. Further, the different advantageous embodiments also may be used to perform inspections of components for aircraft 200 during maintenance and service 114.

One or more of the advantageous embodiments take into account and recognize that it would be desirable to have a method and apparatus to monitor for corrosion. The different advantageous embodiments also recognize and take into account that it would be desirable to have a method and apparatus for detecting corrosion that may be performed in a nondestructive manner. Further, the different advantageous embodiments recognize and take into account that it would be desirable to detect corrosion earlier than possible with currently available techniques.

The different advantageous embodiments provide a method and apparatus for inspecting locations in an object for corrosion. In some advantageous embodiments, an apparatus may have a housing, an excitation unit mounted to the housing, and a detector mounted to the housing. In these illustrative examples, the housing may be portable. The housing may also be capable of being positioned by a human operator relative to a location on an object. This location may contain quantum dots. The excitation unit may be capable of sending energy into the location in which the energy is capable of causing a response from the quantum dots present in the location. The detector is capable of detecting the response from the quantum dots in the location.

Figure 3:
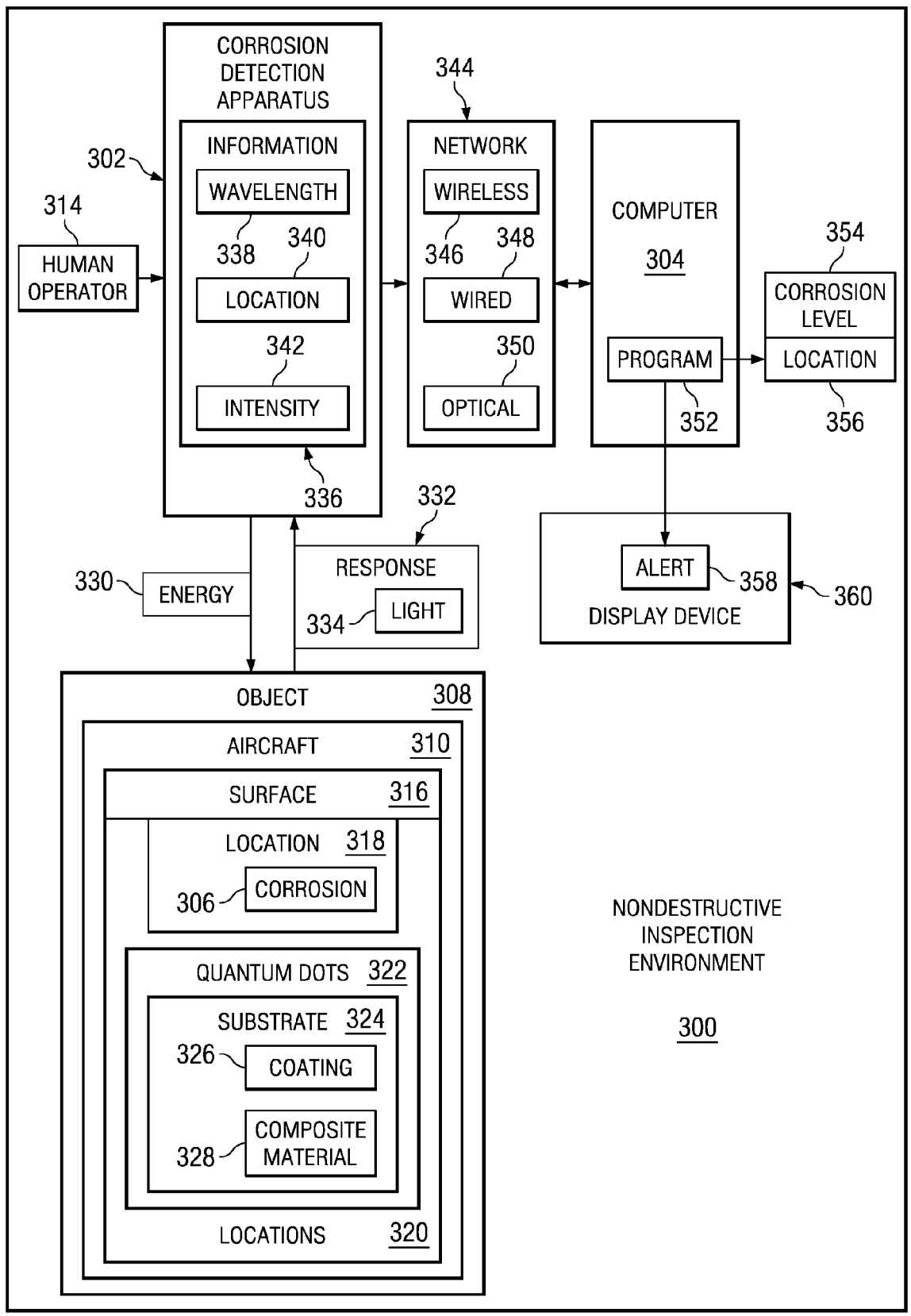
FIG. 3 is a diagram of a monitoring environment in accordance with an advantageous embodiment.

With reference now to FIG. 3, a diagram of a monitoring environment is depicted in accordance with an advantageous embodiment. In this example, nondestructive inspection environment 300 may include corrosion detection apparatus 302 and computer 304. These components may be used in nondestructive inspection environment 300 to detect corrosion 306 for object 308. In these illustrative examples, object 308 may take the form of aircraft 310. Aircraft 310 may be an aircraft such as, for example, aircraft 200 in FIG. 2.

In these illustrative examples, corrosion 306 may refer to a breaking down of properties in the material in an object due to chemical reactions with the surroundings around the object. For example, corrosion 306 may occur with a loss of electrons of metals. This loss may occur from a metal reacting with water and oxygen. This reaction forms free hydrogen+, H+. Corrosion 306 also may be a wearing and/or thickness in a material in the surface of an object; a crack, a fracture, and/or break in the surface material of an object; and/or erosion in the material in the surface of the object.

Corrosion 306 may be caused by exposure to weather, heat, corrosive chemicals, rust, energy, light, an oxidation process, and/or exposure to any other corrosive substance or process that may result in destruction and/or wearing of a surface material and/or surface coating on an object. For example, a crack in paint may expose a substrate of a structure to moisture, which may result in corrosion 306.

Corrosion detection apparatus 302, in these examples, is portable. For example, corrosion detection apparatus 302 may be manipulated by human operator 314. Human operator 314 may move and/or position corrosion detection apparatus 302, with respect to surface 316 of aircraft 310, in location 318 within locations 320 in aircraft 310. As another example, corrosion detection apparatus 302 may be, for example, positioned at a first location within locations 320, operated to perform corrosion inspection, and then moved to a new location within locations 320 and positioned to perform corrosion inspection at the new location.

Surface 316 may be an exterior and/or interior surface with respect to aircraft 310. For example, surface 316 may be a surface of a wing panel on the exterior of the aircraft. In other advantageous embodiments, surface 316 may be, for example, a cavity within the aircraft, such as a structure within the wing of aircraft 310.

In these illustrative examples, the detection of corrosion 306 is performed using quantum dots 322. Quantum dots 322 may be located on and/or in substrate 324 for aircraft 310. Substrate 324 may be, for example, coating 326 located on surface 316 in locations 320. In other advantageous embodiments, substrate 324 may be part of aircraft 310. For example, substrate 324 may take the form of composite material 328, which may be used in aircraft 310 to form various structures such as, for example, without limitation, a spar, a fuselage, a wing panel, an aileron, a flap, or some other suitable structure.

In these illustrative examples, a quantum dot is a semiconductor element whose excitations are confined in three-dimensional spatial dimensions. Quantum dots 322 are capable of being designed to emit a response after having been exposed to free electrons and/or free hydrogen+. The free hydrogen+ may be a hydrogen+ atom freed from a water molecule. This response is light in these illustrative examples.

For example, the response may be different after quantum dots 322 have been exposed to free hydrogen+ as compared to when quantum dots 322 have not been exposed to free hydrogen+. The free hydrogen+ may be produced during a chemical reaction that causes corrosion 306. Further, in some advantageous embodiments, quantum dots 322 may provide a different response when exposed to air as opposed to when embedded in a material. In these different advantageous embodiments, quantum dots 322 may have a shape in the form of a sphere.

Human operator 314 positions corrosion detection apparatus 302 on surface 316 at location 318 in locations 320 of aircraft 310. When corrosion detection apparatus 302 is positioned, energy 330 is transmitted by corrosion detection apparatus 302 into surface 316 at location 318.

Response 332 is detected by corrosion detection apparatus 302 in response to transmitting energy 330. Response 332 may take the form of light 334. Light 334 is detected by corrosion detection apparatus 302.

Corrosion detection apparatus 302 identifies information 336 about light 334. Light 334 may be visible and/or may not be visible. Information 336 may include, for example, without limitation, wavelength 338, location 340, and intensity 342. Information 336 may be transmitted to computer 304. In these illustrative examples, the transmission of information 336 is over network 344.

Network 344 may take various forms. For example, network 344 may be wireless 346, wired 348, optical 350, and/or some other suitable type of network. In the illustrative examples, network 344 may be wireless 346. This type of network may increase the flexibility and capability of moving and/or positioning corrosion detection apparatus 302.

Information 336 may be processed using program 352 executing in computer 304. Of course, in other advantageous embodiments, information 336 may be viewed directly from the output of corrosion detection apparatus 302 when corrosion detection apparatus 302 takes the form of a camera or some other suitable type of detection device.

Intensity 342 may be used to identify the amount of corrosion. For example, as intensity 342 increases, an inference can be made that corrosion 306 is greater than when compared to a lower level of intensity 342. Further, quantum dots 322 may be designed to change intensity 342 based on the level of corrosion 306.

Program 352 determines whether corrosion 306 is present in any of locations 320 using information 336. Program 352 may store corrosion level 354 in association with location 356.

Further, program 352 may generate alert 358, which may be presented on display device 360. Alert 358 also may be presented in other manners. For example, alert 358 may take the form of a text message, an email message, or some other suitable mechanism for alert 358.

In these illustrative examples, human operator 314 may perform corrosion detection inspections with corrosion detection apparatus 302, while the aircraft is on the ground, or even in service. For example, human operator 314 may operate corrosion detection apparatus 302 on the interior of aircraft 310, while aircraft 310 is in flight. Human operator 314 may operate corrosion detection apparatus 302, while aircraft 310 is on the ground in between flights or when maintenance is performed on aircraft 310.

In this manner, corrosion detection apparatus 302 may be used to monitor for corrosion 306 in aircraft 310 without requiring destructive testing. Further, corrosion detection apparatus 302 also may perform nondestructive inspections in a manner that may be more accurate than visual inspections performed by human operator 314. Corrosion detection apparatus 302 detects response 332, which may have a different value for wavelength 338 if corrosion 306 is present.

The illustration of FIG. 3 is not meant to imply physical or architectural limitations to the manner in which different advantageous embodiments may be implemented. Some advantageous embodiments may have other components in addition to, or in place of, the ones illustrated. In yet other advantageous embodiments, some of the illustrated components may be unnecessary.

For example, nondestructive inspection environment 300 may include additional corrosion detection apparatuses in addition to corrosion detection apparatus 302. In this manner, multiple operators may perform inspections of aircraft 310 to determine more quickly whether corrosion 306 is present than with a single device.

In some advantageous embodiments, corrosion detection apparatus 302 may be moved and/or positioned by a robotic arm, a machine, or some other suitable device. Further, in some advantageous embodiments, network 344 may be unnecessary. With this type of implementation, corrosion detection apparatus 302 may communicate directly with computer 304 through a cable and/or wireless interface.

Figure 4:
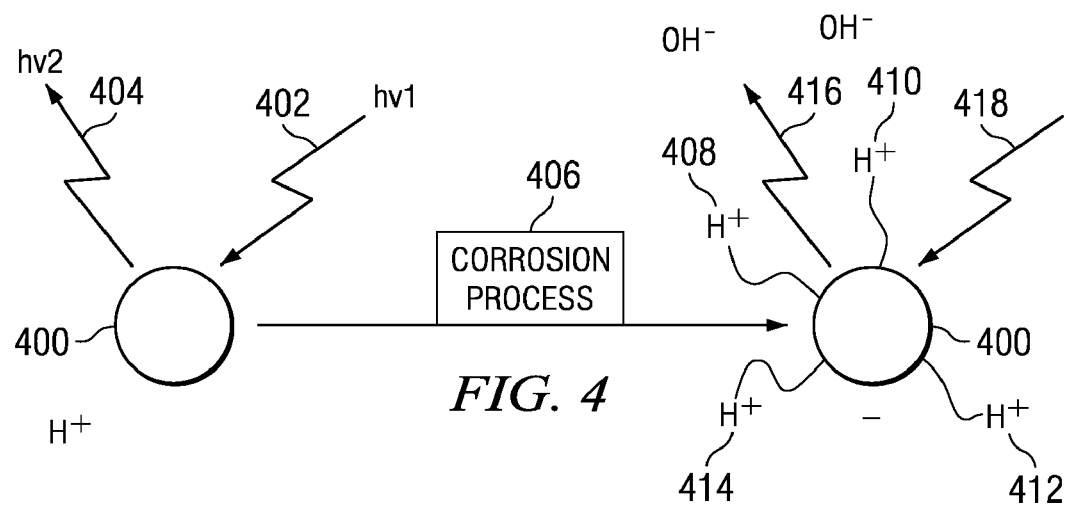
FIG. 4 is a diagram illustrating the responses generated by a quantum dot in accordance with an advantageous embodiment.

With reference now to FIG. 4, a diagram illustrating the responses generated by a quantum dot is depicted in accordance with an advantageous embodiment. In this example, quantum dot 400 is an example of a quantum dot in quantum dots 322 in FIG. 3.

Quantum dot 400 may receive energy 402 from an energy source such as, for example, without limitation, a laser beam. In response, quantum dot 400 may emit light 404. Light 404, emitted by quantum dot 400, has a wavelength and/or intensity when no corrosion is present.

When corrosion occurs, corrosion process 406 may expose quantum dot 400 to free hydrogen+, such as free hydrogen+ 408, 410, 412, and 414. This free hydrogen+ may occur from a reaction of water with the substrate. Corrosion process 406 may occur when moisture and/or some other fluid acting as an electrolyte comes into contact with an object in the aircraft. This contact may occur, for example, without limitation, through a scratch, an abraded area, and/or penetration of the paint and/or primer coating.

Exposure to free hydrogen+ 408, 410, 412, and 414 may result in hydrogen+ 408, 410, 412, and 414 being attracted to and/or attached to quantum dot 400. This attachment causes quantum dot 400 to emit light 416 when exposed to energy 418. Light 416 may have a different wavelength and/or intensity as compared to light 404 because of exposure of quantum dot 400 to free hydrogen+ 408, 410, 412, and 414. Light 416 may have a different wavelength if one or more of free hydrogen+ 408, 410, 412, and/or 414 bond to quantum dot 400.

In these illustrative examples, the emission of light 416 may occur only when quantum dot 400 has free hydrogen+ 408, 410, 412, and 414 attached to quantum dot 400 and when energy 418 has a specific or selected wavelength. In other words, if energy 418 has a wavelength outside of the selected wavelength, quantum dot 400 may not generate light 416.

As a result, quantum dot 400 may only generate light 416 when energy 418 is applied to quantum dot 400 and free hydrogen+ 408, 410, 412, and 414 have become attached to quantum dot 400. In this illustrative example, four free hydrogen+ atoms are shown attached to quantum dot 400. Of course, the generation of light 416 may occur with other numbers of free hydrogen+ atoms being attached to quantum dot 400. For example, light 416 may be generated when one free hydrogen+ atom, two free hydrogen+ atoms, 18 free hydrogen+ atoms, or some other number of free hydrogen+ atoms are attached to quantum dot 400.

With the use of quantum dots, such as quantum dot 400, the detection of light 416, when corrosion process 406 has occurred, may provide a capability to measure very small amounts of corrosion caused by corrosion process 406. These small amounts of corrosion may be much smaller than the amounts of corrosion required for detecting a material loss that is used to produce the corrosion that is currently detectable by current processes.

Figure 5:
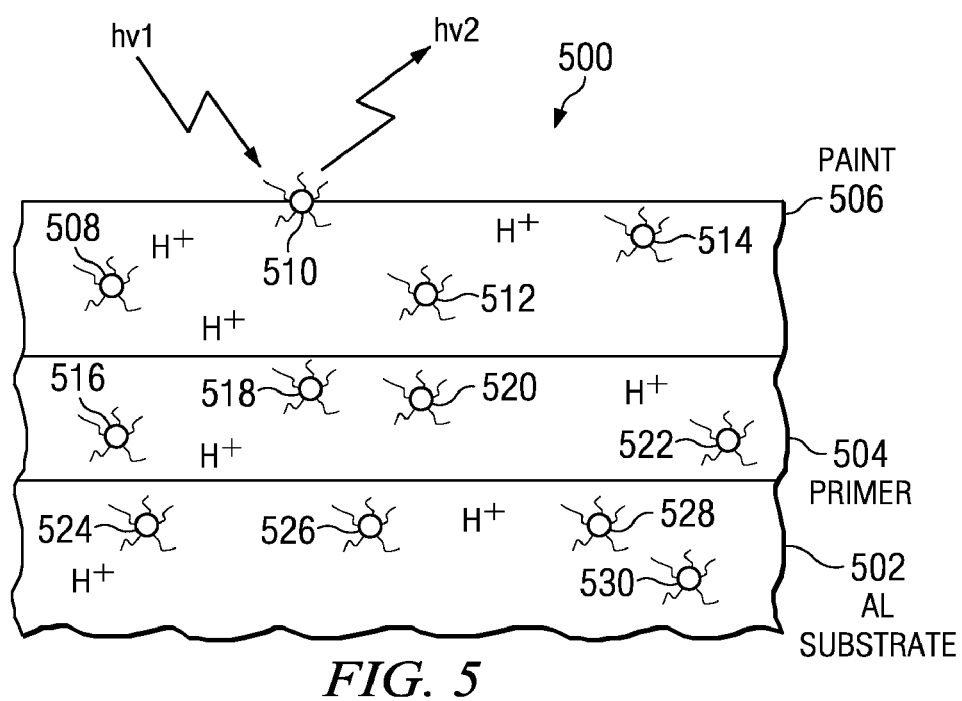
FIG. 5 is a diagram illustrating quantum dots in a location for an object in accordance with an advantageous embodiment.

Turning now to FIG. 5, a diagram illustrating quantum dots in a location for an object is depicted in accordance with an advantageous embodiment. In this example, a portion of object 500 is depicted in accordance with an advantageous embodiment. Object 500 is an example of a portion of object 308 in FIG. 3. In this illustrative example, object 500 includes substrate 502, primer layer 504, and paint layer 506.

In these examples, quantum dots may be present in at least one of substrate 502, primer layer 504, and paint layer 506. As used herein, the phrase "at least one of", when used with a list of items, means that different combinations of one or more of the items may be used and only one of each item in the list may be needed. For example, "at least one of item A, item B, and item C" may include, for example, without limitation, item A, or item A and item B. This example also may include item A, item B, and item C, or item B and item C.

In this illustrative example, quantum dots 508, 510, 512, and 514 are present in paint layer 506. Quantum dots 516, 518, 520, and 522 are present in primer layer 504. Quantum dots 524, 526, 528, and 530 are present within substrate 502. In the different advantageous embodiments, these quantum dots may be manufactured using any known and/or currently available process for manufacturing, producing, and/or otherwise generating quantum dots.

In this example, quantum dots are shown as being present in the different layers in object 500. Depending on the particular implementation, the quantum dots may be present in only one layer or some other combination of layers. Further, quantum dots also may be placed into a polymer coating specifically for use in corrosion detection.

The different advantageous embodiments recognize that quantum dots may be associated with object 500 in a number of different ways. As illustrated in these examples, quantum dots may be embedded directly into substrate 502. Substrate 502 may be, for example, an aluminum substrate, a composite substrate, and/or some other suitable type of material. When used in primer layer 504 and/or paint layer 506, quantum dots may be prepared colloidally. In this manner, the quantum dots may be free floating and attached to various molecules via metal coordinating functional groups.

These groups include, but are not limited to, thiol, amine, nitrile, phosphine, phosphine oxide, phosphonic acid, carboxylic acid, and/or other ligands. This capability to attach to other molecules greatly increases the flexibility of quantum dots with respect to the types of environments in which they can be applied. By bonding appropriate molecules to the surface of a commodity, the quantum dots can be dispersed or dissolved in nearly any solvent or incorporated into a variety of inorganic and organic films. In addition, the surface chemistry can be used to effectively alter the properties of the quantum dots, including the brightness and electronic lifetimes of the quantum dots.

The different quantum dots may be selected to emit light in different wavelengths, resulting in different colors. This type of implementation may be used to identify the location of different quantum dots. For example, quantum dots in paint layer 506 may be selected to emit a different light color when exposed to free hydrogen+ as compared to quantum dots in primer layer 504, which may generate a different wavelength of light when exposed to free hydrogen+.

In other words, the wavelength of light emitted from a quantum dot may be related to the size and/or material used for quantum dots. Quantum dots may be tunable, such that the signals or wavelengths emitted by a quantum dot can be selected and/or adjusted by changing the size of the quantum dot and/or changing the composition of the material in the quantum dot.

For example, the emission wavelength and, consequently, the color of light emitted by the quantum dot, can be altered simply by changing the size of the quantum dot. Smaller quantum dots yield smaller or shorter wavelengths that tend to fall more within the blue color range of light. Larger quantum dots emit longer wavelengths of light, which produces a red-colored light emission.

Quantum dots of different sizes can be tethered and/or linked together to form molecules, attached to a polymer backbone, linked or tethered to form chains, and/or linked to form lattices. Each quantum dot in these chains and/or lattices that are of differing sizes will emit different wavelengths of light. In this manner, different sized quantum dots can be linked together to form lattices of quantum dots that will emit different colored lights in different patterns.

In other words, a grouping of quantum dots of different sizes and/or types may result in a pattern of light in which each of the quantum dots in the molecule emits light with a different wavelength. These different wavelengths, when emitted by the molecule, form the pattern for the molecule.

Further, multiple sized quantum dots may be mixed together and then linked. This mixture may result in a pattern being present in a response generated by the quantum dots. This response may be multi-colored and can be identified by a unique quantum dot pattern in a fashion similar to a barcode. Thus, a quantum dot barcode with specific fluoroscopic characteristics may be selectively or uniformly embedded into the material used to manufacture an object or into a coating applied to the object.

Figure 6:
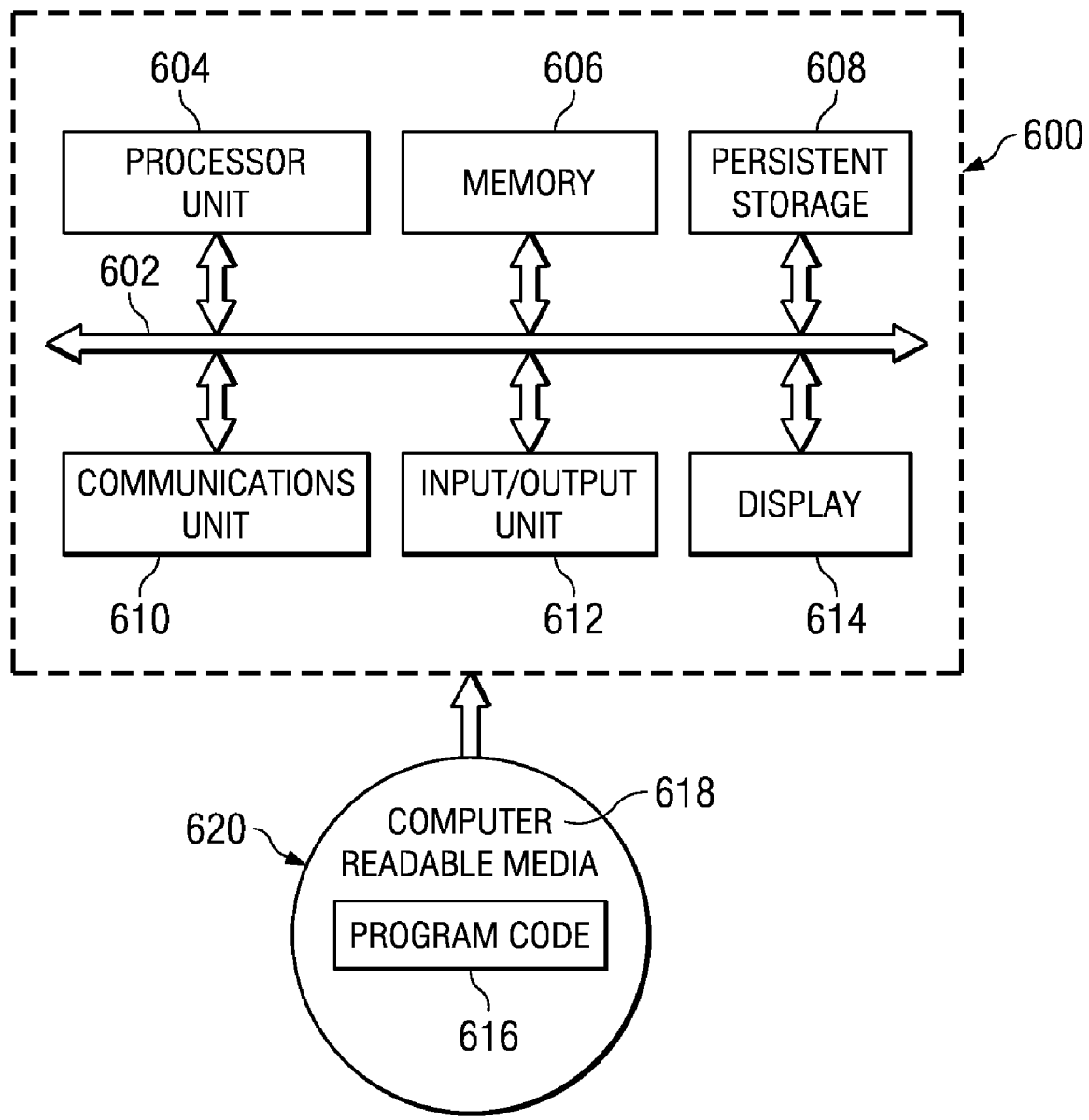
FIG. 6 is a diagram of a data processing system in accordance with an advantageous embodiment.

Turning now to FIG. 6, a diagram of a data processing system is depicted in accordance with an advantageous embodiment. Data processing system 600 is an example of a data processing system that may be used to implement computer 304 in FIG. 3. In this illustrative example, data processing system 600 includes communications fabric 602, which provides communications between processor unit 604, memory 606, persistent storage 608, communications unit 610, input/output (I/O) unit 612, and display 614.

Processor unit 604 serves to execute instructions for software that may be loaded into memory 606. Processor unit 604 may be a set of one or more processors or may be a multi-processor core, depending on the particular implementation. Further, processor unit 604 may be implemented using one or more heterogeneous processor systems in which a main processor is present with secondary processors on a single chip. As another illustrative example, processor unit 604 may be a symmetric multi-processor system containing multiple processors of the same type.

Memory 606 and persistent storage 608 are examples of storage devices. A storage device is any piece of hardware that is capable of storing information either on a temporary basis and/or a permanent basis. Memory 606, in these examples, may be, for example, a random access memory or any other suitable volatile or non-volatile storage device.

Persistent storage 608 may take various forms, depending on the particular implementation. For example, persistent storage 608 may contain one or more components or devices. For example, persistent storage 608 may be a hard drive, a flash memory, a rewritable optical disk, a rewritable magnetic tape, or some combination of the above. The media used by persistent storage 608 also may be removable. For example, a removable hard drive may be used for persistent storage 608.

Communications unit 610, in these examples, provides for communications with other data processing systems or devices. In these examples, communications unit 610 is a network interface card. Communications unit 610 may provide communications through the use of either or both physical and wireless communications links.

Input/output unit 612 allows for input and output of data with other devices that may be connected to data processing system 600. For example, input/output unit 612 may provide a connection for user input through a keyboard and mouse. Further, input/output unit 612 may send output to a printer. Display 614 provides a mechanism to display information to a user.

Instructions for the operating system and applications or programs are located on persistent storage 608. These instructions may be loaded into memory 606 for execution by processor unit 604. The processes of the different embodiments may be performed by processor unit 604 using computer-implemented instructions, which may be located in a memory, such as memory 606. These instructions are referred to as program code, computer usable program code, or computer readable program code that may be read and executed by a processor in processor unit 604. The program code in the different embodiments may be embodied on different physical or tangible computer readable media, such as memory 606 or persistent storage 608.

Program code 616 is located in a functional form on computer readable media 618 that is selectively removable and may be loaded onto or transferred to data processing system 600 for execution by processor unit 604. Program code 616 and computer readable media 618 form computer program product 620 in these examples. In one example, computer readable media 618 may be in a tangible form such as, for example, an optical or magnetic disk that is inserted or placed into a drive or other device that is part of persistent storage 608 for transfer onto a storage device, such as a hard drive, that is part of persistent storage 608.

In a tangible form, computer readable media 618 also may take the form of a persistent storage, such as a hard drive, a thumb drive, or a flash memory, that is connected to data processing system 600. The tangible form of computer readable media 618 is also referred to as computer recordable storage media. In some instances, computer readable media 618 may not be removable.

Alternatively, program code 616 may be transferred to data processing system 600 from computer readable media 618 through a communications link to communications unit 610 and/or through a connection to input/output unit 612. The communications link and/or the connection may be physical or wireless in the illustrative examples. The computer readable media also may take the form of non-tangible media, such as communications links or wireless transmissions containing the program code.

In some advantageous embodiments, program code 616 may be downloaded over a network to persistent storage 608 from another device or data processing system for use within data processing system 600. For instance, program code stored in a computer readable storage medium in a server data processing system may be downloaded over a network from the server to data processing system 600. The data processing system providing program code 616 may be a server computer, a client computer, or some other device capable of storing and transmitting program code 616.

The different components illustrated for data processing system 600 are not meant to provide architectural limitations to the manner in which different embodiments may be implemented. The different advantageous embodiments may be implemented in a data processing system including components in addition to or in place of those illustrated for data processing system 600.

Other components shown in FIG. 6 can be varied from the illustrative examples shown. The different embodiments may be implemented using any hardware device or system capable of executing program code. As one example, the data processing system may include organic components integrated with inorganic components and/or may be comprised entirely of organic components excluding a human being. For example, a storage device may be comprised of an organic semiconductor.

As another example, a storage device in data processing system 600 is any hardware apparatus that may store data. Memory 606, persistent storage 608, and computer readable media 618 are examples of storage devices in a tangible form.

In another example, a bus system may be used to implement communications fabric 602 and may be comprised of one or more buses, such as a system bus or an input/output bus. Of course, the bus system may be implemented using any suitable type of architecture that provides for a transfer of data between different components or devices attached to the bus system. Additionally, a communications unit may include one or more devices used to transmit and receive data, such as a modem or a network adapter. Further, a memory may be, for example, memory 606 or a cache such as found in an interface and memory controller hub that may be present in communications fabric 602.

Figure 7:
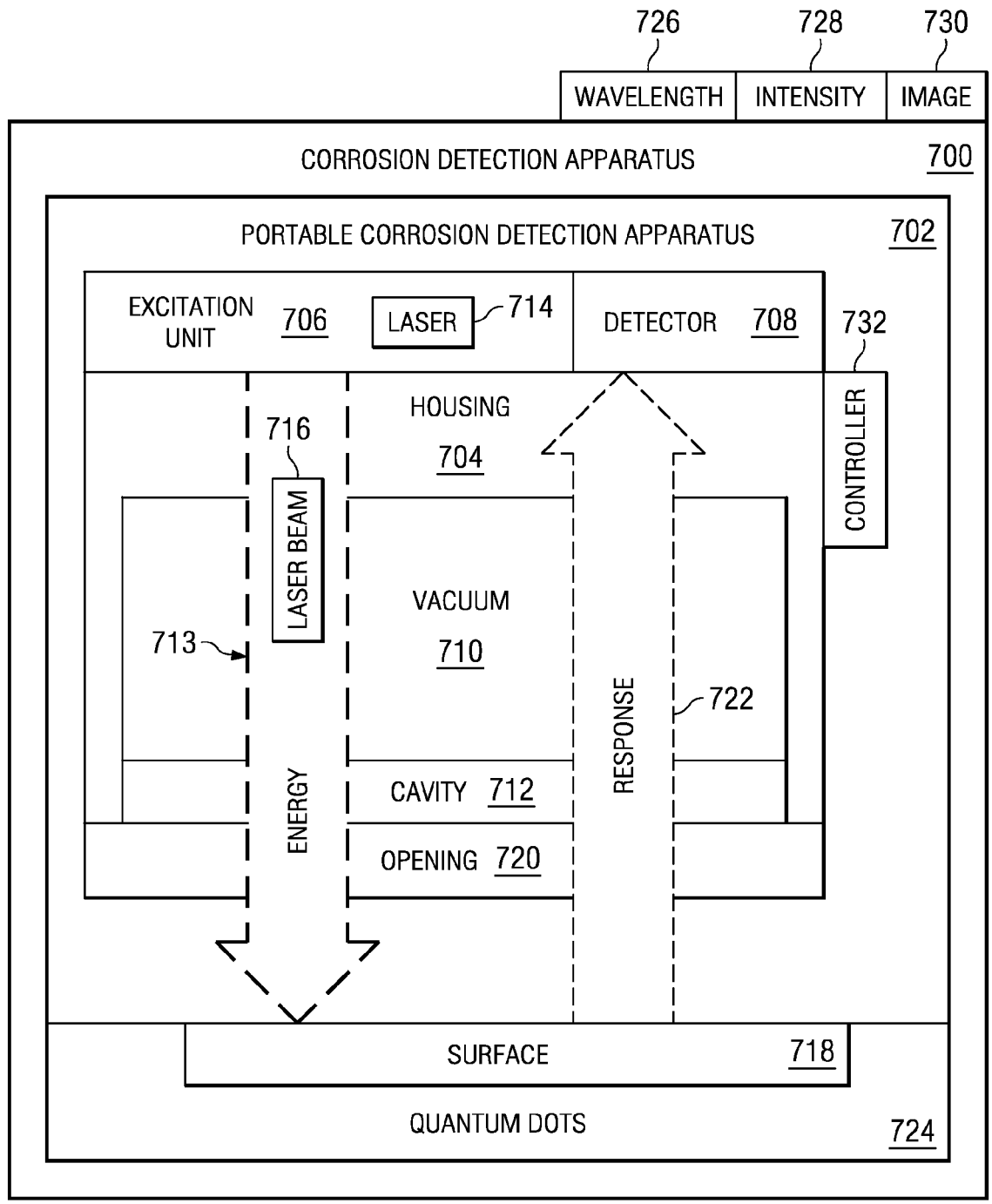
FIG. 7 is a diagram of a corrosion detection apparatus in accordance with an advantageous embodiment.

With reference next to FIG. 7, a diagram of a corrosion detection apparatus is depicted in accordance with an advantageous embodiment. Corrosion detection apparatus 700 is an example of corrosion detection apparatus 302 in FIG. 3.

In this illustrative example, corrosion detection apparatus 700 takes the form of portable corrosion detection apparatus 702. In other words, portable corrosion detection apparatus 702 may be moved and/or positioned, for example, by a human operator, for use in inspecting an object, such as aircraft 200 in FIG. 2.

In this illustrative example, portable corrosion detection apparatus 702 includes housing 704, excitation unit 706, and detector 708. Housing 704 is designed to be capable of creating vacuum 710 within cavity 712 in housing 704. A vacuum unit (not shown) or other methods known in the art may be connected to the housing to create a vacuum in the cavity. Vacuum 710 may reduce and/or prevent defective moisture, pollution, and other unwanted components from entering cavity 712. Further, housing 704 may be comprised of a material that may shield cavity 712 from unwanted radiation. For example, housing 704 may be comprised of aluminum with a coating of flat black paint. In another example, housing 704 may be comprised of a composite material. This type of configuration of housing 704 may reduce a need for a narrow-band pass optical filter, which may reduce signal intensity.

Excitation unit 706 is capable of generating energy 713 for use in performing nondestructive inspection of an object. Energy 713 may be directed towards quantum dots 724 that may be in the location in which nondestructive inspection is performed. In these illustrative examples, excitation unit 706 may be implemented using laser 714, which may generate energy 713 in the form of laser beam 716. Laser beam 716 may be directed towards surface 718 through opening 720 in housing 704.

In response to laser beam 716, response 722 may be generated by quantum dots 724. Quantum dots 724 may be on and/or below surface 718.

Response 722 may be detected by detector 708. Response 722 may be used to identify wavelength 726, intensity 728, and other suitable parameters from response 722. This information may be identified by sending information about response 722 to a remote data processing system, such as a computer or a monitor. For example, response 722 may be sent in the form of image 730.

In other advantageous embodiments, controller 732 may be capable of controlling the generation of laser beam 716 and the detection of response 722 by detector 708. Further, controller 732 may be present in corrosion detection apparatus 700 and may process the data to identify information such as, for example, without limitation, wavelength 726, intensity 728, and other suitable information. In other embodiments, identification of such information may be performed in the detector, or other processor within the housing or remote from the housing.

The illustration of portable corrosion detection apparatus 702 in FIG. 7 is not meant to imply physical or architectural limitations to the manner in which different advantageous embodiments may be implemented. Some components may be included in addition to, or in place of, others illustrated in FIG. 7. In yet other advantageous embodiments, some components may be unnecessary. For example, controller 732 may be unnecessary if the information about response 722 is sent directly to a remote computer. Further, instead of using controller 732, an external device also may control the generation of laser beam 716, depending on the particular implementation.

The detection system employed within portable corrosion detection apparatus 702 may be implemented using a number of different detection mechanisms. For example, foster resonance energy transfer, laser excitation pump, and probe with phase lock detection and gated imaging are examples of some techniques that may be used in implementing excitation unit 706 and detector 708 for portable corrosion detection apparatus 702. Essentially, any technique and/or device having a capability to detect a shift in a wavelength of a quantum dot may be used.

Figure 8:
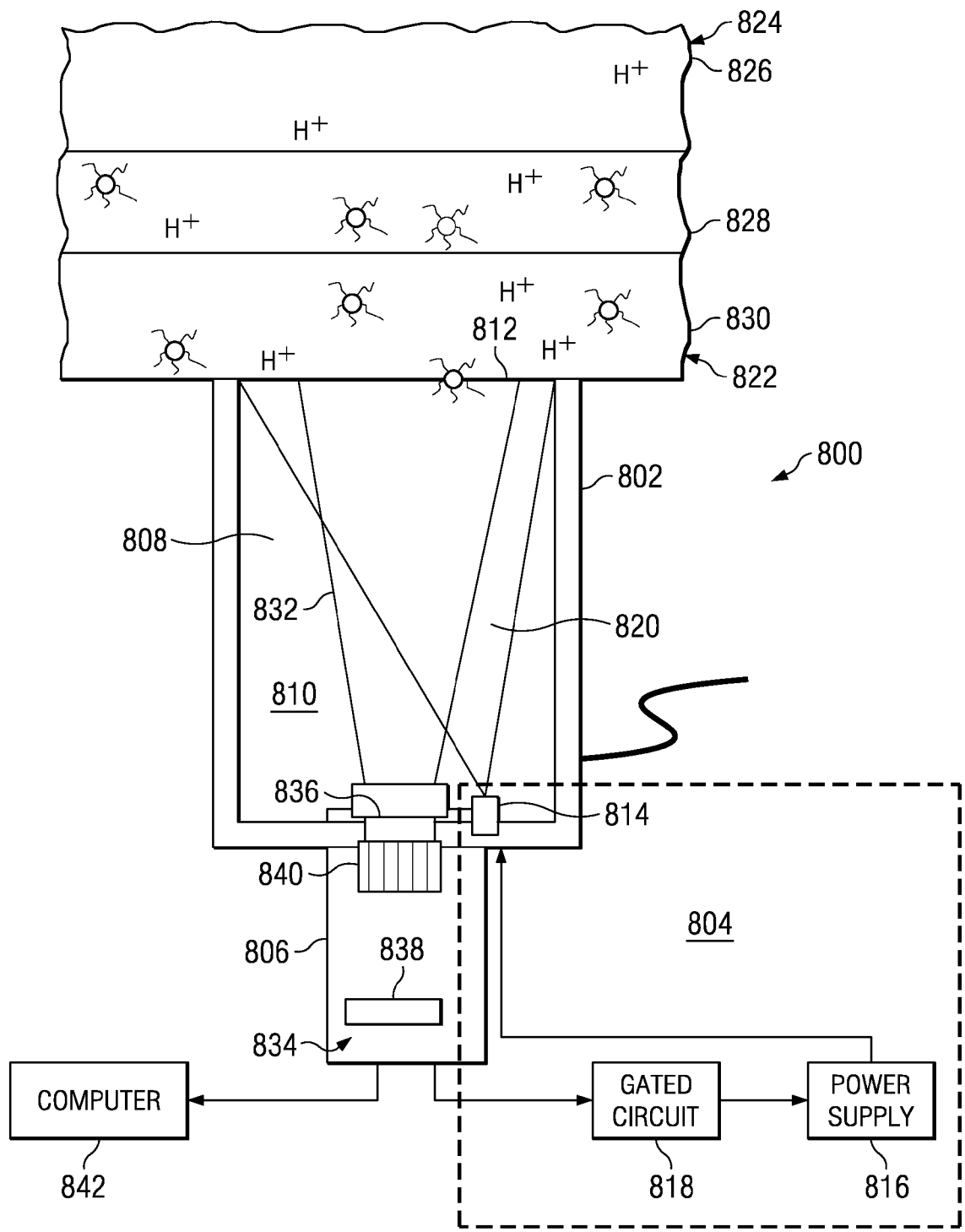
FIG. 8 is a diagram of a portable corrosion detection apparatus in accordance with an advantageous embodiment.

Turning now to FIG. 8, a diagram of a portable corrosion detection apparatus is depicted in accordance with an advantageous embodiment. In this example, portable corrosion detection apparatus 800 is an example of one implementation for portable corrosion detection apparatus 702 in FIG. 7. In this example, portable corrosion detection apparatus 800 may include housing 802, excitation unit 804, and detector 806.

Housing 802 takes the form of vacuum chamber 808 having cavity 810 and opening 812 in this illustrative example. In this depicted example, excitation unit 804 may be capable of transmitting energy to perform an inspection for corrosion. As illustrated, excitation unit 804 includes light source 814, power supply 816, and gated circuit 818. Light source 814 may be, for example, at least one of a laser, a laser diode, a light-emitting diode, an arc lamp, a fluorescent lamp, an incandescent lamp, and/or some other suitable light source. Power supply 816 may provide power to cause light source 814 to generate beam 820. Gated circuit 818 may control power supply 816 to selectively generate beam 820. Gated circuit 818 may control power supply 816 to synchronize excitation and de-excitation of quantum dots by beam 820.

In this example, opening 812 may be placed onto surface 822 of object 824. Object 824 may include aluminum layer 826, primer layer 828, and paint layer 830. In this example, response 832 is generated by beam 820 being projected onto surface 822. Response 832 may be detected by detector 806.

In this example, detector 806 may include light intensifying camera 834 and optics 836. Optics 836 may direct response 832 into light intensifying camera 834. Although detector 806 is illustrated using intensifying camera 834 in this example, other types of detectors may be used. For example, a photo sensor, camera, or low-light detection camera may be employed in detector 806.

Light intensifying camera 834 may generate an image of the response that may be sent to computer 842 for analysis. Further, light intensifying camera 834 may take the form of a gated camera that may control gated circuit 818 to control the generation of beam 820 by light source 814.

In these different illustrative examples, light intensifying camera 834 may be implemented using any commercially available light intensifying camera. For example, compact intensified charged-coupled device (CCD) cameras from Hamamatsu Corporation may be used. For example, a C10054 series of compact intensified charged-coupled device cameras available from Hamamatsu Corporation may be employed. Of course, other types of detectors may be used for detector 806. For example, detector 806 may be implemented using a charge injection device (CID) camera, a complementary metal oxide semiconductor (CMOS) camera, an infrared camera, and/or some other suitable type of camera or detector.

Light intensifying camera 834 may include optics 836, micro-channel plate 838, and fiber bundle image transfer and image transfer system 840. Optics 836 may be capable of directing response 832 to micro-channel plate 838. Micro-channel plate 838 is a device that is capable of detecting and amplifying low-light level images. For example, micro-channel plate 838 may be a planar component used for the detection of particles, such as electrons or ions and impinging radiation. Micro-channel plate 838 may be similar to an electron multiplier and may be used to intensify response 832.

A low-light level may be, for example, the amount of light present during night. Micro-channel plate 838 may be capable of creating an image by detecting single photons. Of course, any type of detection device capable of detecting response 832, as generated by quantum dots, may be used. In some advantageous embodiments, micro-channel plate 838 may be unnecessary when a low light camera is used in place of light intensifying camera 834 for detector 806.

Information generated by detector 806 may be sent to computer 842 for analysis. In these examples, the transfer of information to computer 842 may be through a cable, optical fiber, wireless transmission system, or some other suitable system.

The illustration of portable corrosion detection apparatus 800 in FIG. 8 is only provided as one example of an implementation of portable corrosion detection apparatus 702 in FIG. 7 and is not meant to imply physical or architectural limitations to the manner in which other advantageous embodiments may be implemented.

For example, in these illustrative examples, light source 814 may take various forms. Light source 814 may be, for example, without limitation, a laser diode, a light-emitting diode, a laser beam, or some other suitable light source. Any light source capable of exciting quantum dots into a higher energy state to generate response 832 may be used.

As another example, computer 842 may be unnecessary. In some advantageous embodiments, portable corrosion detection apparatus 800 may include a processor to process response 832 and/or perform image analysis.

Figure 9:
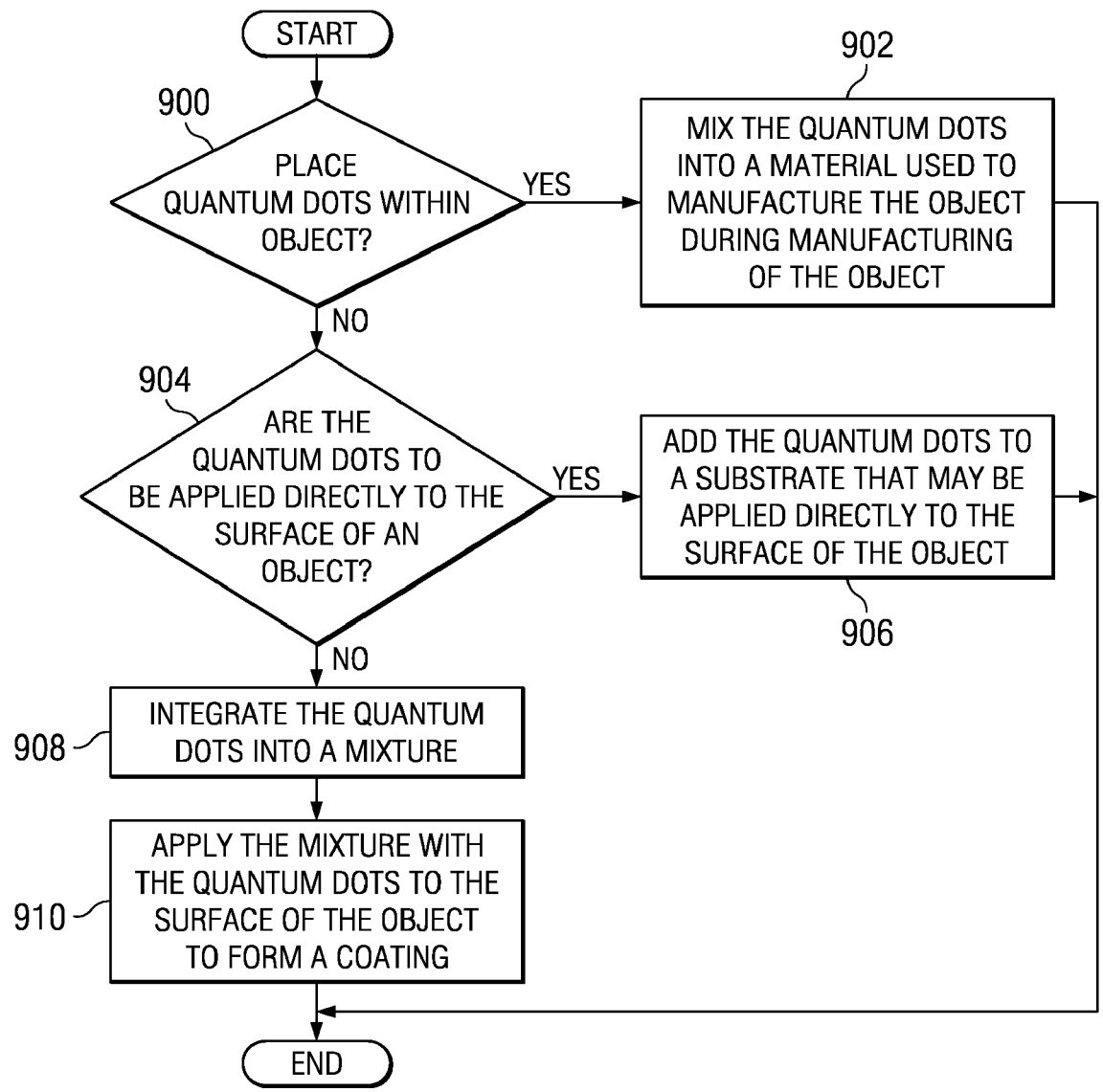
FIG. 9 is a flowchart of a process for associating quantum dots with an object in accordance with an advantageous embodiment.

Turning now to FIG. 9, a flowchart of a process for associating quantum dots with an object is depicted in accordance with an advantageous embodiment. The process illustrated in FIG. 9 may be used to associate quantum dots, such as quantum dots 322 in FIG. 3 for use in monitoring an object, such as object 308 in FIG. 3. This process may be performed during various steps, operations, and/or phases in manufacturing, performing maintenance, refurbishing, and/or otherwise modifying an object. For example, the process illustrated in FIG. 9 may be implemented during component and subassembly manufacturing 106, system integration 108, and/or maintenance and service 114 in FIG. 1. In other words, this process may be used to associate quantum dots with locations in an object.

The process begins by determining whether to place quantum dots within the object (operation 900). If quantum dots are to be placed into the object, the quantum dots may be mixed into a material used to manufacture the object during manufacturing of the object (operation 902), with the process terminating thereafter. In operation 902, quantum dots may be placed into a resin and/or other composite material used for an object that may employ composite parts and/or structures.

With reference again to operation 900, if quantum dots are not to be placed into the object, a determination is made as to whether quantum dots are to be applied directly to the surface of an object (operation 904). If quantum dots are to be applied directly to the surface of the object, the quantum dots are added to a substrate that may be applied directly to the surface of the object (operation 906), with the process terminating thereafter. In operation 906, the quantum dots may be mixed into a solution that may cause the quantum dots to adhere to, bond, and/or otherwise be secured to the surface of the object.

With reference again to operation 904, if the quantum dots are not to be applied directly to the surface of the object, the process integrates the quantum dots into a mixture (operation 908). This mixture may be, for example, a primer, a paint, a sealant, or some other suitable mixture. The mixture with the quantum dots is then applied to the surface of the object to form a coating (operation 910), with the process terminating thereafter.

Figure 10:
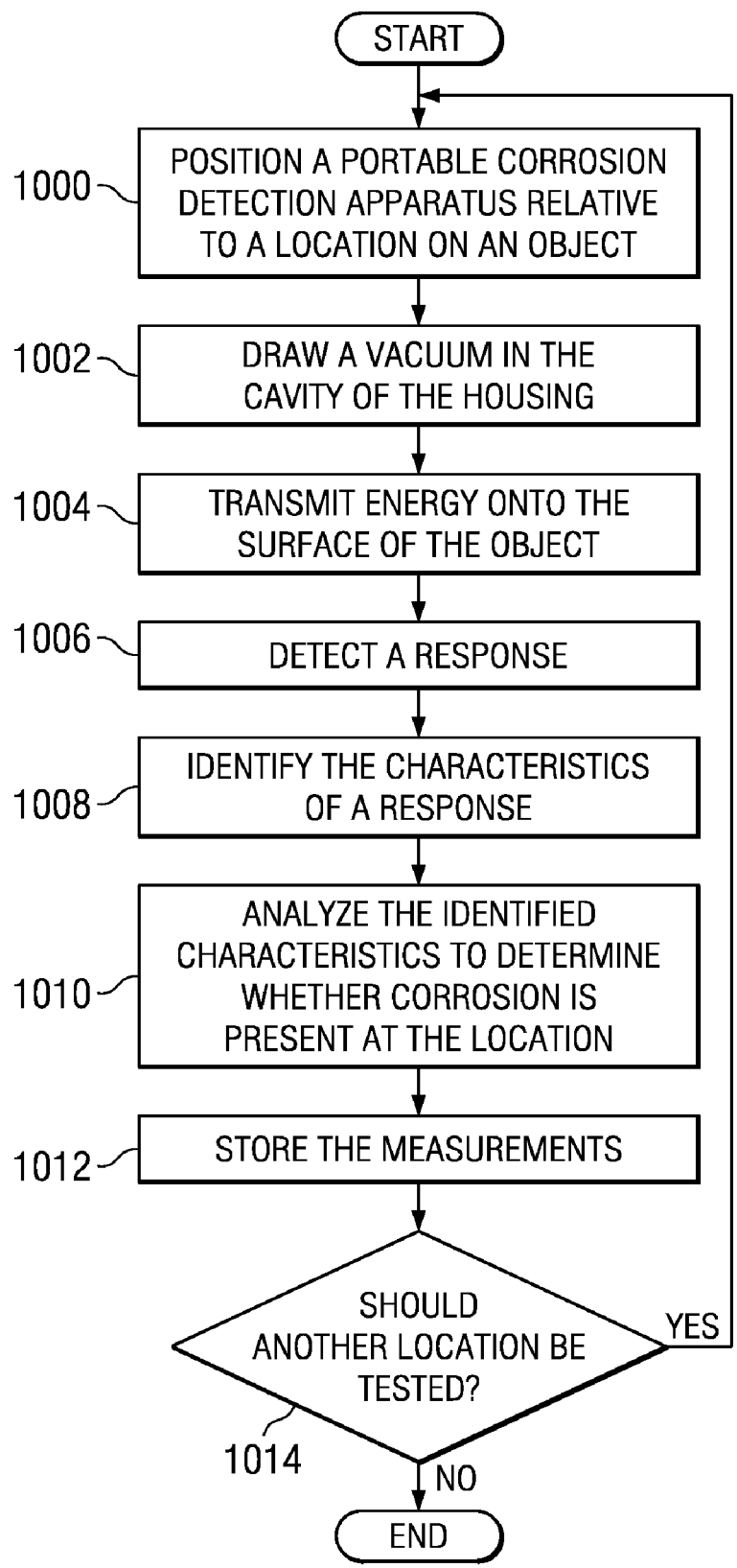
FIG. 10 is a flowchart of a process for testing a surface of an object for corrosion in accordance with an advantageous embodiment.

With reference now to FIG. 10, a flowchart of a process for testing a surface of an object for corrosion is depicted in accordance with an advantageous embodiment. The process illustrated in FIG. 10 may be implemented using a corrosion detection apparatus such as, for example, without limitation, corrosion detection apparatus 700 in FIG. 7. Some of the operations illustrated in FIG. 10 may be implemented using computer 304 in FIG. 3. The positioning and manipulation of the corrosion detection apparatus may be performed by an operator such as, for example, human operator 314 in FIG. 3.

The process may begin by positioning a portable corrosion detection apparatus relative to a location on the object, the location having quantum dots (operation 1000). For example, an opening of the housing for the corrosion detection apparatus may be placed over or onto a surface of an object to be inspected. The process may then draw a vacuum in the cavity of the housing (operation 1002). Energy may be transmitted onto the surface of the object (operation 1004). This energy may be, for example, light with a selected wavelength that is capable of causing a response from quantum dots that may be located on and/or in the surface of the object.

A response is then detected (operation 1006). This response may be light and/or fluorescence at a particular frequency. Characteristics of a response are identified (operation 1008). These characteristics may include, for example, the wavelength and the intensity of the response.

The identified characteristics may be analyzed to determine whether corrosion is present at the location (operation 1010). The measurements may then be stored (operation 1012). Operations 1010 and 1012 may be implemented using a computer, such as computer 304 in FIG. 3. In some advantageous embodiments, a controller located in the corrosion detection apparatus may perform operations 1010 and 1012.

A determination is then made as to whether another location should be tested (operation 1014). If another location should be tested, the process returns to operation 1000. Otherwise, the process terminates.

Figure 11:
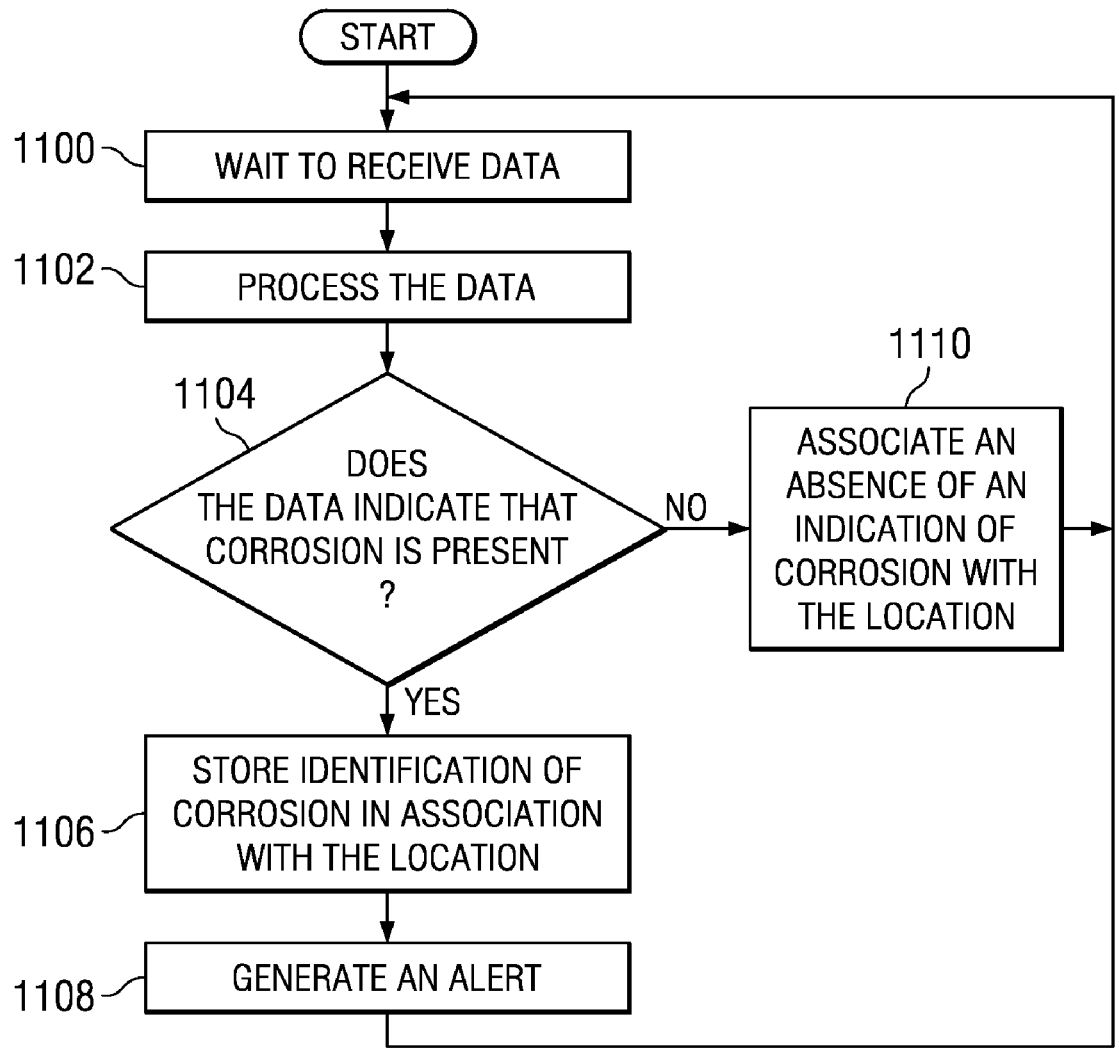
FIG. 11 is a flowchart of a process for determining whether corrosion has occurred in accordance with an advantageous embodiment.

With reference now to FIG. 11, a flowchart of a process for determining whether corrosion has occurred is depicted in accordance with an advantageous embodiment. The process in FIG. 11 may be implemented in nondestructive inspection environment 300 in FIG. 3. More specifically, program 352 executing on computer 304 in FIG. 3 is an example of a software component that may implement this process.

The process begins by waiting to receive data from sensors (operation 1100). When data is received, the process then processes the data (operation 1102). In processing the data, the process may identify a location, strength, intensity, and/or wavelength for the data received. Operation 1102 also may identify other types of information based on the data received. For example, other information may be included, such as environmental information.

A determination is then made as to whether the data indicates that corrosion is present (operation 1104). This determination may be made by identifying the expected wavelength for the quantum dots. In other advantageous embodiments, the determination may be made by determining whether a particular wavelength is present. In these illustrative examples, this determination may compare the wavelength in the data to an expected wavelength that is present when a quantum dot has been exposed to a free hydrogen+ atom. Such a change may indicate that corrosion may be present. In these illustrative examples, the amount of corrosion may be detected based on the intensity of the light. As more corrosion is present, more quantum dots generate light in these examples.

If corrosion is identified as being present, this identification is stored in association with the location (operation 1106). The process also may generate an alert (operation 1108). This alert may be presented on a display device and/or sent in an email, a text message, through a voice prompt, or some other suitable process or device for generating and/or delivering alerts. The process then returns to operation 1100 to wait to receive data from a sensor. With reference again to operation 1104, if the data does not indicate that corrosion is present, the process then associates an absence of an indication of corrosion with the location.

The flowcharts and block diagrams in the different depicted embodiments illustrate the architecture, functionality, and operation of some possible implementations of apparatus and methods in different advantageous embodiments. In this regard, each block in the flowcharts or block diagrams may represent a module, a segment, a function, and/or a portion of an operation or step. In some alternative implementations, the function or functions noted in the blocks may occur out of the order noted in the figures. For example, in some cases, two blocks shown in succession may be executed substantially concurrently, or the blocks may sometimes be executed in the reverse order, depending upon the functionality involved.

For example, in FIG. 10, operation 1010 may be performed after another location is to be tested in operation 1014. As another example, operation 1012 may transmit the measurements to a remote location for processing rather than storing the measurements.

Thus, the different advantageous embodiments may provide a capability to perform nondestructive inspection of an object. The different advantageous embodiments may include an apparatus having a housing, an excitation unit, and a detector. The excitation unit and the detector may be mounted to the housing. In these examples, the housing may be portable and capable of being positioned by a human operator relative to a location on an object in which quantum dots may be present. The excitation unit may be capable of sending energy into the location in which the energy is capable of causing a response from the quantum dots. The detector is capable of detecting the response from the quantum dots in the location.

With one or more of the different advantageous embodiments, nondestructive inspection may be performed in the manner that allows for detection of corrosion much sooner than presently capable with visual inspections by human operators. The different advantageous embodiments may be able to detect corrosion that may have no visible characteristics. The different advantageous embodiments may be capable of detecting free electrons generated by the corrosion process. These free electrons may cause quantum dots in the location to provide a response that indicates the presence of free electrons that have been bonded to the quantum dots. With the apparatus being portable and capable of being positioned by a human operator, inspection of various locations may be performed during maintenance and service by a human operator.

The different advantageous embodiments can take the form of an entirely hardware embodiment, an entirely software embodiment, or an embodiment containing both hardware and software elements. Some embodiments are implemented in software, which includes, but is not limited to, forms such as, for example, firmware, resident software, and microcode.

Furthermore, the different embodiments can take the form of a computer program product accessible from a computer-usable or computer-readable medium providing program code for use by, or in connection with, a computer or any device or system that executes instructions. For the purposes of this disclosure, a computer-usable or computer-readable medium can generally be any tangible apparatus that can contain, store, communicate, propagate, or transport the program for use by, or in connection with, the instruction execution system, apparatus, or device.

The computer-usable or computer-readable medium can be, for example, without limitation, an electronic, magnetic, optical, electromagnetic, infrared, or semiconductor system, or a propagation medium. Non-limiting examples of a computer-readable medium include a semiconductor or solid state memory, magnetic tape, a removable computer diskette, a random access memory (RAM), a read-only memory (ROM), a rigid magnetic disk, and an optical disk. Optical disks may include compact disk-read only memory (CD-ROM), compact disk-read/write (CD-R/W), and DVD.

Further, a computer-usable or computer-readable medium may contain or store a computer-readable or usable program code such that when the computer-readable or usable program code is executed on a computer, the execution of this computer-readable or usable program code causes the computer to transmit another computer-readable or usable program code over a communications link. This communications link may use a medium that is, for example, without limitation, physical or wireless.

A data processing system suitable for storing and/or executing computer-readable or computer-usable program code will include one or more processors coupled directly or indirectly to memory elements through a communications fabric, such as a system bus. The memory elements may include local memory employed during actual execution of the program code, bulk storage, and cache memories which provide temporary storage of at least some computer-readable or computer-usable program code to reduce the number of times code may be retrieved from bulk storage during execution of the code.

Input/output or I/O devices can be coupled to the system either directly or through intervening I/O controllers. These devices may include, for example, without limitation, keyboards, touch screen displays, and pointing devices. Different communications adapters may also be coupled to the system to enable the data processing system to become coupled to other data processing systems or remote printers or storage devices through intervening private or public networks. Non-limiting examples are modems and network adapters and are just a few of the currently available types of communications adapters.

The description of the different advantageous embodiments has been presented for purposes of illustration and description, and it is not intended to be exhaustive or limited to the embodiments in the form disclosed. Many modifications and variations will be apparent to those of ordinary skill in the art. Although illustrative examples have been described with respect to an object in the form of an aircraft, different advantageous embodiments may be applied to other objects.

For example, the object may be selected from one of a mobile platform, a stationary platform, a land-based structure, an aquatic-based structure, a space-based structure, an aircraft, a surface ship, a tank, a personnel carrier, a train, a spacecraft, a space station, a satellite, a submarine, an automobile, a power plant, a bridge, a dam, a manufacturing facility, a building, a cargo bay, a door sill, a landing gear bay, an insulation blank, a bilge, a seat track, a leading edge of a wing, a trailing edge of a wing, a trailing edge of a stabilizer, a fuel tank, and/or some other suitable object.

Further, different advantageous embodiments may provide different advantages as compared to other advantageous embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:
1. An apparatus comprising:
 a housing, wherein the housing is portable and capable of being positioned relative to a location on an object, wherein quantum dots are present in the location;
 an excitation unit mounted to the housing, wherein the excitation unit is capable of sending energy into the location in which the energy is capable of causing a response from the quantum dots; and a detector mounted to the housing, wherein the detector is capable of detecting the response from the quantum dots exposed to hydrogen+ in the location.

2. The apparatus of claim 1 further comprising:
a processor unit, wherein the detector is in communication with the processor unit and wherein the processor unit is capable of determining whether corrosion is present in the location.

3. The apparatus of claim 1, wherein the excitation unit is selected from at least one of a light source, a light-emitting diode, and a laser diode.

4. The apparatus of claim 1, wherein the detector is selected from at least one of a photo sensor, a camera, and a light intensifying camera.

5. The apparatus of claim 1, wherein the detector generates an image of the response.

6. The apparatus of claim 1, wherein the detector generates an identification of a wavelength for the response.

7. The apparatus of claim 1, wherein the detector comprises:
optics; and
a photo sensor capable of detecting the response.

8. The apparatus of claim 1, wherein the housing has a cavity and further comprising:
a vacuum unit connected to the housing, wherein the vacuum unit is capable of creating a vacuum in the cavity.

9. The apparatus of claim 1, wherein the location is associated with the quantum dots exposed to hydrogen+ present in the location by at least one of being attached to a surface of the location, being located within a coating on the location, being located on the surface of the location, and being embedded within a material comprising the object.

10. The apparatus of claim 1, wherein the object is selected from one of a mobile platform, a stationary platform, a land-based structure, an aquatic-based structure, a space-based structure, an aircraft, a surface ship, a tank, a personnel carrier, a train, a spacecraft, a space station, a satellite, a submarine, an automobile, a power plant, a bridge, a dam, a manufacturing facility, a building, a cargo bay, a door sill, a landing gear bay, an insulation blank, a bilge, a seat track, a leading edge of a wing, a trailing edge of a wing, a trailing edge of a stabilizer, and a fuel tank.

11. The apparatus of claim 1, wherein the hydrogen+ is attached to the quantum dot.

12. The apparatus of claim 11, wherein the attachment of hydrogen+ to the quantum dot configures the quantum dot to emit light when exposed to energy.

13. The apparatus of claim 1, wherein the hydrogen+ is attracted to the quantum dot.

14. The apparatus of claim 1, wherein the detector is configured to detect an intensity of the response from the quantum dot.

15. A method for detecting corrosion on an object, the method comprising:
positioning a portable corrosion detection apparatus relative to a location on the object, wherein quantum dots are present in the location;
sending energy into the location; and
detecting the response from the quantum dots exposed to hydrogen+ in the location.

16. The method of claim 15 further comprising:
drawing a vacuum in a cavity within a housing.

17. The method of claim 15 further comprising:
placing the quantum dots in the location.

18. The method of claim 17, wherein the placing step comprises:
applying a coating containing the quantum dots to a surface of the object.

19. The method of claim 15 further comprising:
determining whether corrosion is present to form a result.

20. The method of claim 19 further comprising:
associating the result with the location.

21. The method of claim 20 further comprising:
storing the result associated with the location.

22. The method of claim 19 further comprising:
performing a maintenance operation based on the result.

23. The method of claim 15, wherein the portable corrosion detection apparatus comprises:
a housing, wherein the housing is portable and capable of being positioned relative to the location on the object, wherein the quantum dots exposed to hydrogen+ are present in the location;
an excitation unit mounted to the housing, wherein the excitation unit is capable of sending energy into the location in which the energy is capable of causing a response from the quantum dots; and
a detector mounted to the housing, wherein the detector is capable of detecting the response from the quantum dots in the location.

24. The method of claim 23, wherein the excitation unit is selected from at least one of a light source, a light-emitting diode, and a laser diode.

25. The method of claim 23, wherein the detector is selected from at least one of a photo sensor, a camera, and a light-intensifying camera.

26. The method of claim 23, wherein the housing has a cavity and further comprising:
a vacuum unit connected to the housing, wherein the vacuum unit is capable of creating a vacuum in the cavity.

27. The method of claim 15 further comprising detecting a response from the quantum dot exposed to hydrogen+.

28. The method of claim 27 wherein the attachment of hydrogen+ to the quantum dot configures the quantum dot to emit light when exposed to energy.

29. The method of claim 27 further comprising detecting an intensity of the response from the quantum dot.

* * * * *